(12) United States Patent
Stuart

(10) Patent No.: US 8,814,035 B2
(45) Date of Patent: Aug. 26, 2014

(54) DOSE INDICATOR

(75) Inventor: Adam J. Stuart, Loughborough (GB)

(73) Assignee: 3M Innovative Properties Company, St. Paul, MN (US)

( * ) Notice: Subject to any disclaimer, the term of this patent is extended or adjusted under 35 U.S.C. 154(b) by 148 days.

(21) Appl. No.: 13/514,192

(22) PCT Filed: Dec. 6, 2010

(86) PCT No.: PCT/US2010/059019
§ 371 (c)(1),
(2), (4) Date: Jun. 6, 2012

(87) PCT Pub. No.: WO2011/071788
PCT Pub. Date: Jun. 16, 2011

(65) Prior Publication Data
US 2012/0241527 A1    Sep. 27, 2012

(30) Foreign Application Priority Data
Dec. 9, 2009   (GB) .................................. 0921555.9

(51) Int. Cl.
*G06C 3/00*        (2006.01)
*G06F 17/00*       (2006.01)

(52) U.S. Cl.
USPC ....................................... 235/87 R; 235/375

(58) Field of Classification Search
CPC .......... A61M 15/0065; A61M 15/009; A61M 2012/0051; A61M 2202/064; B65D 83/54; B65D 83/75; G06M 1/06; G06M 1/26; G06M 3/025; G06M 3/12
USPC ........................................ 235/87 R, 375, 381
See application file for complete search history.

(56) References Cited

U.S. PATENT DOCUMENTS

| 5,349,945 | A |  | 9/1994 | Wass et al. |
| 5,871,007 | A |  | 2/1999 | Clark, Jr. |
| 6,752,153 | B1 |  | 6/2004 | Eckert |
| 8,113,199 | B2 | * | 2/2012 | Augustyn et al. ........ 128/205.23 |
| 8,459,253 | B2 | * | 6/2013 | Howgill ................... 128/200.23 |
| 8,479,732 | B2 | * | 7/2013 | Stuart et al. .............. 128/205.23 |
| 2005/0161467 | A1 | * | 7/2005 | Jones .............................. 222/23 |
| 2013/0291861 | A1 | * | 11/2013 | Stuart et al. .............. 128/200.23 |

FOREIGN PATENT DOCUMENTS

| DE | 10 2006 049 614 | 4/2008 |
| GB | 2 372 541 | 8/2002 |
| WO | WO 93/24167 | 12/1993 |
| WO | WO 98/56444 | 12/1998 |
| WO | WO 99/36115 | 7/1999 |
| WO | WO 99/57019 | 11/1999 |
| WO | WO 00/59806 | 10/2000 |
| WO | WO 2004/041334 | 5/2004 |
| WO | WO 2005/060535 | 7/2005 |
| WO | WO 2006/062450 | 6/2006 |
| WO | WO 2007/124406 | 11/2007 |
| WO | WO 2009/037085 | 3/2009 |
| WO | WO 2011/063067 | 5/2011 |

* cited by examiner

*Primary Examiner* — Thien M Le

(57) ABSTRACT

A dose counter is described. The dose counter may be used, for instance, in a medical inhaler device.

25 Claims, 10 Drawing Sheets

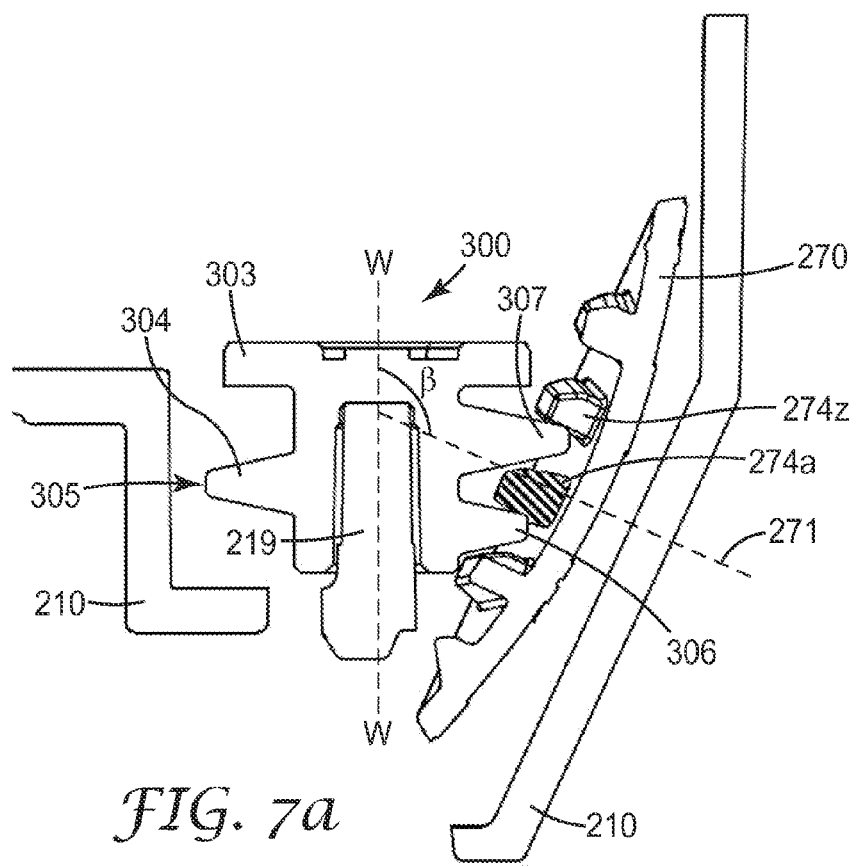
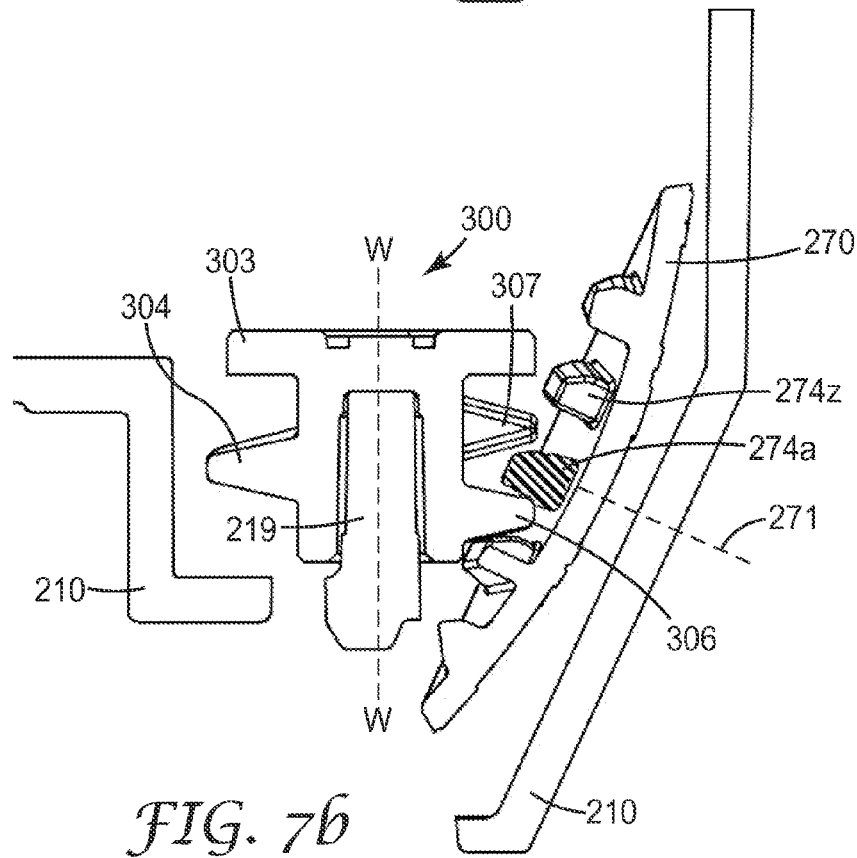

DOSE INDICATOR

CROSS REFERENCE TO RELATED APPLICATIONS

This application is a national stage filing under 35 U.S.C. 371 of PCT/US2010/059019, filed Dec. 6, 2010, which claims priority to United Kingdom Application No. 0921555.9, filed Dec. 9, 2009, the disclosure of which is incorporated by reference in its/their entirety herein.

FIELD

This invention relates to dose counters for dispensers and in particular to dose counters for use with metered dose inhalers comprising a container for medicament equipped with a reciprocal actuation means, such as a valve, to dispense a dose of medicament from the container.

BACKGROUND

Since the metered dose pressurised inhaler was introduced in the mid-1950's, inhalation has become a widely used route for delivering bronchodilator drugs and steroids to the airways of asthmatic patients. More recently, inhalation from a pressurised inhaler has been a route selected for administration of other drugs that are not primarily concerned with treatment of a bronchial malady.

A pressurised metered dose inhaler generally comprises an aerosol container equipped with a metered dose dispensing valve (which is generally herein referred to as a canister) and an actuator. The actuator generally comprises a nozzle block to retain the canister (typically the valve stem of the metering valve) and a user-port such as a mouthpiece, as well as an optional, but typically used, cylindrical housing for housing the aerosol container. The aerosol container contains a pressurised aerosol formulation that generally comprises a liquefied propellant and a medicament and, if desired and/or needed, one or more excipients such as a surfactant or a solvent. The medicament may be in the form of a dispersion or in solution in the aerosol formulation. Metered dose dispensing valves generally comprise a valve stem that is moved inwardly with respect to the container to dispense a metered dose of aerosol formulation. The canister is inserted into the actuator with the valve stem engaging the nozzle block of the actuator. In use, a patient places their lips round the mouthpiece and presses the base of the aerosol container causing the container to move relative to the valve stem to fire a dose of medicament through the mouthpiece.

One of the disadvantages arising from the use of such known inhalers is that the patient cannot readily determine the amount of medicament in the container at any given time. In an extreme case this could mean that a patient in need of a dose of medicament might find that the inhaler will not dispense a dose because its contents have already been exhausted.

There have been many proposals for dose counters for use with metered dose inhalers, in particular pressurised metered dose inhalers, including e.g. dose counters described in DE 10 2006 049 614 (RPC Formatec GmbH), WO 2000/59806 (Allsop et al.), WO 1998/56444 (Rand et al.), U.S. Pat. No. 5,349,945 (Wass et al.), U.S. Pat. No. 5,871,007 (Clark), WO 1999/36115 (Blacker et al.), WO 1999/57019 (Grychowski et al.), WO 2004/041334 (Bang & Olufsen), WO 2005/060535 (Purkins et al.), WO 2007/124406 (Stuart et al.), WO 06/062450 (Hörlines) and WO 1993/024167 (Holroyd). Some are mounted onto the base of the aerosol container (e.g. WO 1999/57019), some are mounted onto the ferrule of the aerosol container (e.g. WO 1998/56444) and others are retained within the interior of the actuator beneath the aerosol container in the space near and or around the nozzle block (e.g. WO 2007/124406 and WO 2005/060535).

SUMMARY OF INVENTION

Incorporation of the type of dose counters retained within the interior of the actuator beneath the aerosol container in the space near and/or around the nozzle block is generally advantageous in that the use of such dose counters can allow for the provision of an inhaler without any change—other than the provision of a dose-indication—from the perspective of the users, said users often being quite conservative and anxious about any change. Moreover a dose counter retained within the interior of the actuator can allow for the provision of an inhaler without any change in form or size, if the size of the dose counter is small enough to be located entirely in the space beneath the aerosol container near and/or around the nozzle block. It has been found challenging to provide high-count dose counters (counters that can count 200-plus counts) that are small enough to fit in the aforementioned space, while at the same time providing a dose counter which has for the general user readable indicia and is desirably robust.

Accordingly one aspect of the present invention provides a dose counter for use with an inhaler comprising a container for medicament equipped with a reciprocal actuation means to dispense a dose of medicament therefrom, said reciprocal actuation means operating along a first axis, the dose counter comprising an indicator member rotatable about a second axis, wherein the indicator member is constructed and arranged to undergo predetermined count-indicating motion when one or more doses are dispensed and wherein the second axis is disposed at an obtuse angle with respect to the first axis, and a worm rotatable about a worm axis, wherein the worm is configured and arranged to drive the indicator member and wherein the worm axis and the second axis do not intersect and are not disposed in a perpendicular alignment relative to each other.

By configuring and arranging an indicator member at an obtuse angle relative to the first axis (the axis of the actuation) where the indicator member is driven by a worm, whose axis is not perpendicular to the axis of rotation of the indicator member, it has been found that one may provide desirably small dose counters that can count and indicate usage of 200-plus doses and at the same time which may be desirably robust e.g. in manufacture and/or in effective usage.

To further minimize usage of space, in particular to minimize the overall length of the dose counter along the first axis, favourably the worm axis and first axis are not coaxial. To yet further facilitate effective/efficient dose count actuation in a minimum of space, generally it is favourable to arrange the counter such that the worm axis is disposed from an angle of 180 degrees ("exact parallel alignment") to an angle of 160 degrees with respect to the first axis, more favourably the worm axis is in parallel alignment to the first axis. In such embodiments where worm axis is in parallel alignment to the first axis, since the first and second axes are disposed at an obtuse angle relative to one another, the second axis is also disposed at an obtuse angle with respect to the worm axis.

Desirably the first and second axes intersect. Desirably the first and worm axes do not intersect.

To yet further facilitate the provision of a compact size and/or robustness, the first and second axes are favourably disposed at an obtuse angle of 145 degrees or less relative to each other, more favourably 135 degrees or less relative to each other, even more favourably 125 degrees or less relative to each other, most favourably 120 degrees or less relative to each other. The first and second axes are favourably disposed at an obtuse angle of 95 degrees or greater relative to each other, more favourably 100 degrees or greater relative to each other, even more favourably 105 degrees or greater relative to each other, most favourably 110 degrees or greater relative to each other.

Favourably the indicator member comprises a region for interaction with the worm, wherein this region of the indicator member and the worm are desirably configured and arranged such that at least one portion of the region of the indicator member meshes with at least one portion of the thread of the worm. It has been found advantageous to configure and arrange this region of the indicator member like a worm wheel. Such a worm wheel may be a separate component affixed to the indicator member or indirectly coupled to the indicator member or such a worm wheel may be integral to the indicator member.

To facilitate the effective and efficient driving of the indicator member by the worm, relative to the angle between the worm axis and second axis, the cross-sectional radius of the worm from the worm axis to the outer edge of the worm flight (thread) favourably generally increases along the worm axis. The cross-sectional diameter of the worm shaft may favourably generally increase along the worm axis and/or the cross-sectional width of the worm thread perpendicular to the worm axis may favourably generally increase along the worm axis.

A further aspect of the present invention includes an actuator for use with or as part of a dispenser, said actuator comprising a dose counter as described herein. Favourably the dose counter is mounted within the interior of the actuator.

Other aspects of the present invention include a dispenser comprising a dose counter as described herein and a dispenser comprising an actuator as described herein. Favourably such a dispenser may be a metered dose dispenser, more favourably a metered dose inhaler, and most favourably a pressurised metered dose inhaler.

In particular favoured embodiments of pressurized metered dose inhalers comprising dose counters as described herein, desirably the dose counter is mounted within the interior of the actuator such that in use, the dose counter is generally positioned beneath the aerosol container (or the canister including said container and metering valve) and/or around a nozzle block of the actuator.

Other favoured embodiments will be apparent from the dependent claims.

The above summary of the present invention is not intended to describe each disclosed embodiment or every implementation of the present invention. The description that follows more particularly exemplifies illustrative embodiments.

BRIEF DESCRIPTION OF DRAWINGS

By way of example only, embodiments of the present invention will now be described below with reference to the accompanying drawings.

DETAILED DESCRIPTION

It is to be understood that the present invention covers all combinations of particular, suitable, desirable, favourable, advantageous and preferred aspects of the invention described herein.

Figure 1:
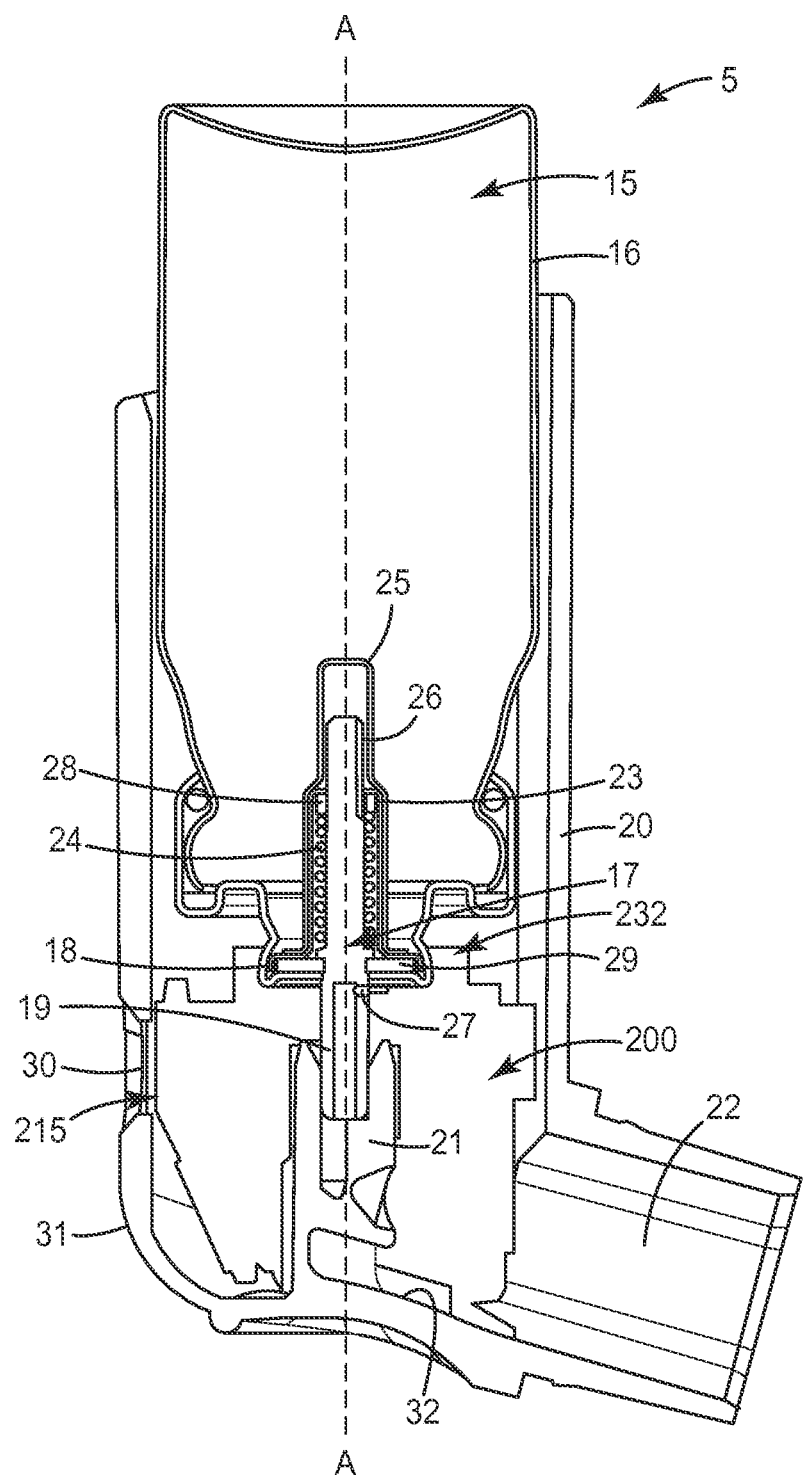
FIG. 1 is a schematic, and in part diagrammatic, illustration of a vertical cross-section through an exemplary pressurized metered dose inhaler.

For better understanding of the present invention, an illustrative, exemplary pressurized metered dose inhaler will be first described. FIG. 1 provides a schematic illustration of a vertical cross-section through an exemplary pressurized metered dose inhaler (5). The illustrated pressurised metered dose inhaler (5) comprises the following components: a canister (15), an actuator (20) and a dose counter (200). The dose counter is only shown diagrammatically with its outer profile in an outline form, and advantageously it is a dose counter in accordance with the present invention, in particular the exemplary dose counter illustrated in FIG. 2 or alternatively the dose counter illustrated in FIG. 3 (both discussed in detail infra)). The canister (15) includes an aerosol container (16) equipped with a metering valve (17) secured via a ferrule (18). The metering valve (17) includes inter alia a valve stem (19), generally a valve body (23) defining a metering chamber, and a spring (24). The metering valve (17) may also include an outer valve body (25) serving as a bottle emptier and/or defining a pre-metering chamber. Although not shown in the illustration, the container (16) typically contains an aerosol formulation that generally comprises at least one active agent (such as at least one medicament) and liquefied propellant (e.g. HFA 134a and/or HFA 227), and optionally one or more excipients. The actuator (20) and canister (15) are arranged so that the valve stem (19) engages with a nozzle block (21) provided within the actuator so that the canister is thus retained in the actuator. In use (when the aerosol container indeed contains a medicament aerosol formulation), the user actuates the pressurized metered dose inhaler (5) to dispense a single dose of medication via the mouthpiece (22) by pressing down on the container (16). Due to the fact that the valve stem (19) is held fixed by the nozzle block and the container (16) moves downwardly when the user presses down on it (thus compressing the valve spring (24)), there is a relative reciprocal movement between the metering valve stem and the container. On this actuation (outward) stroke, once the container moves sufficiently downwards an inner groove (26) of the valve stem (19) passes an inner gasket seal (28) so that the metering chamber is sealed off, and once the container moves further sufficiently downwards an opening (27) of the outer portion of the valve stem (19) passes an outer gasket (29) into the metering chamber so that the metering valve will fire (dispense) a metered dose of medicament-containing formulation (i.e. that quantity of formulation in the metering chamber). After actuation, once the user releases the container, the container on its return stroke will move (under the force of the expansion of the valve spring) upwardly relative to the valve stem back to its position of rest. The longitudinal axis of reciprocal movement between the metering valve and the aerosol container is labelled "A" (i.e. the first axis and also sometimes referred to as the actuation axis). As illustrated, the dose counter (200) is mounted within the interior of the actuator (20), generally positioned beneath the container near and around the nozzle block (21). As shown in FIG. 1, the dose counter may be provided with a window (215) to allow sight of indicia, where the indicia may be viewed through a window (30) in the actuator back wall (31). Alternatively, a dose counter may be provided with a transparent housing, allowing for sighting of indicia without necessarily having to provide a window in the dose counter. The dose counter once mounted desirably remains in position within the actuator, even when the canister (15) is removed, so that the dose counter may not be removed by the user of the inhaler.

Dose counters described herein may also used in connection with actuators (e.g. nasal actuators) for use with a canister including an aerosol container and a metering valve fitted with a dip tube. In particular in connection with such actuators and canisters, desirably the dose counter is mounted within the interior of the actuator, such that, in use, the dose counter is generally positioned above the container near and/or around a nozzle block of the actuator.

As noted above, the present invention relates to dose counters for use in connection with dispensers, in particular to dose counters for use with dispensers for metered dispensing of a medication. In the description and illustrations herein, orientation references such as top, bottom, above, below, vertical, horizontal, upwardly, downwardly, beneath, above and the like are not intended to be limiting in nature, but only to provide visual references for the reader. It is understood that dose counters described herein will function in any orientation, e.g. in an orientation as illustrated herein (e.g. as in FIG. 2) or upside down. As indicated above, dose counters described herein may be mounted within the interior of an actuator, in particular such that the dose counter is beneath the container. Once again the term "beneath" is not intended to be limiting in nature, and it will be appreciated that in an upside down orientation or in the event of operation in such an opposite orientation the dose counter will be then "above" the container.

Figure 2:
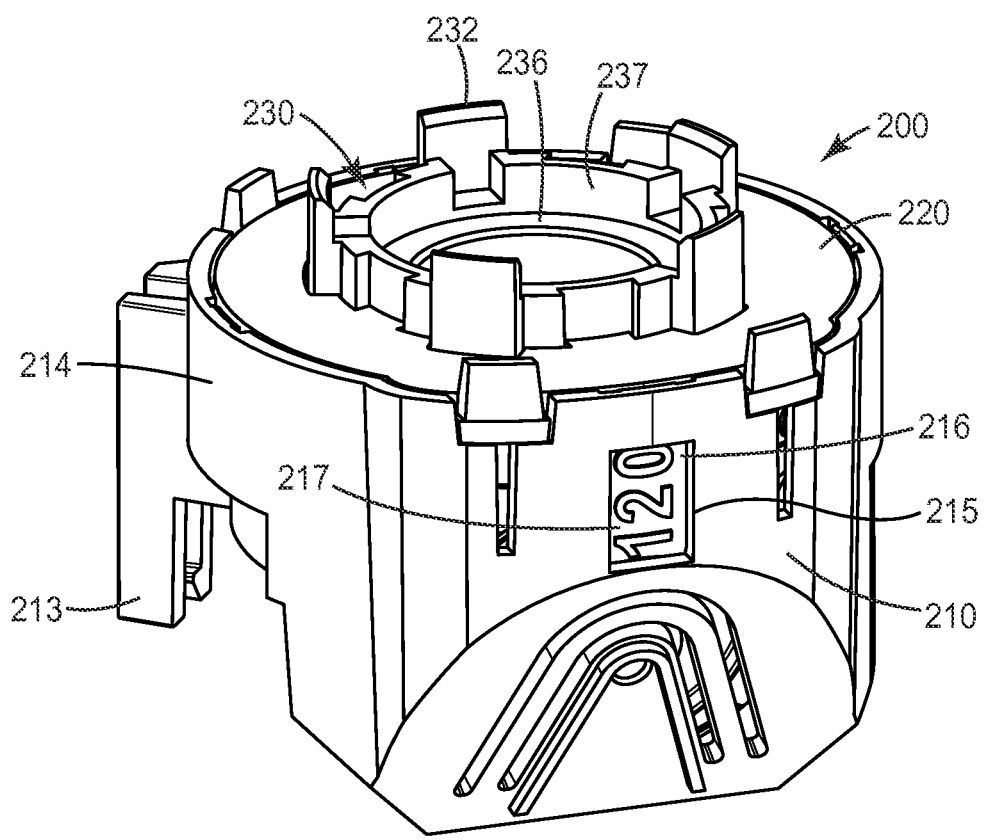
FIG. 2 is a perspective illustration of an exemplary dose counter in accordance with the present invention.

FIG. 2 is a perspective illustration of an exemplary dose counter in accordance with the present invention. As can be appreciated from FIG. 2, the working components of the dose counter (200) are contained within a housing (210) and retained by a lid (220), where essentially just indicia (216) are visible via a window (215). Alternatively, the complete housing may be provided in a transparent material, such that the indicia may be viewed through the sidewall (214) of the dose counter housing. Such an exemplary dose counter is illustrated in FIGS. 3 to 8, where the housing is made of a transparent material and no window is provided in the housing.

Figure 3:
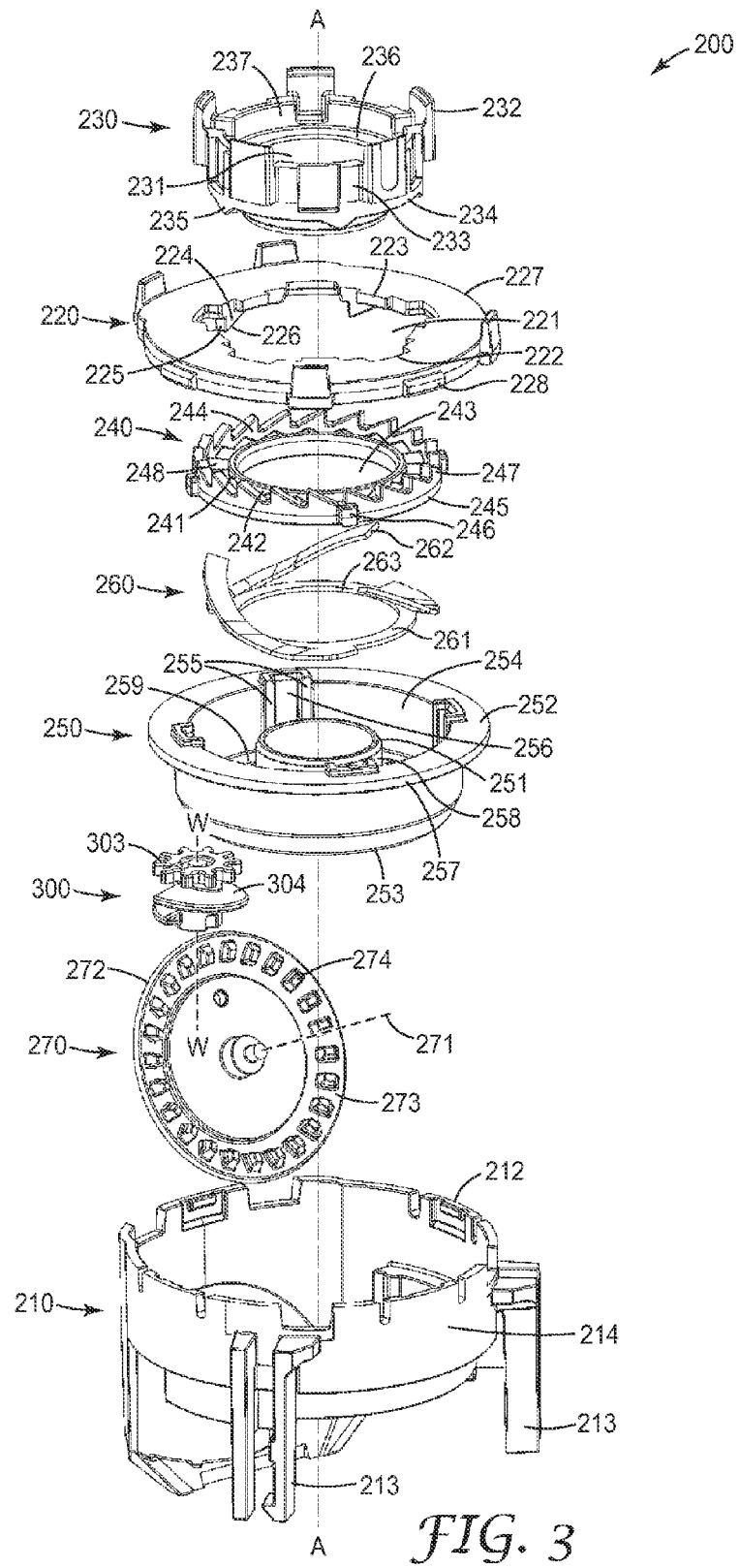
FIG. 3 represents an exploded view of another exemplary dose counter in accordance with the present invention. The dose counter illustrated in FIG. 3 differs from the embodiment illustrated in FIG. 2 in that no window is provided in the housing and the housing of the counter is transparent.
Figure 4:
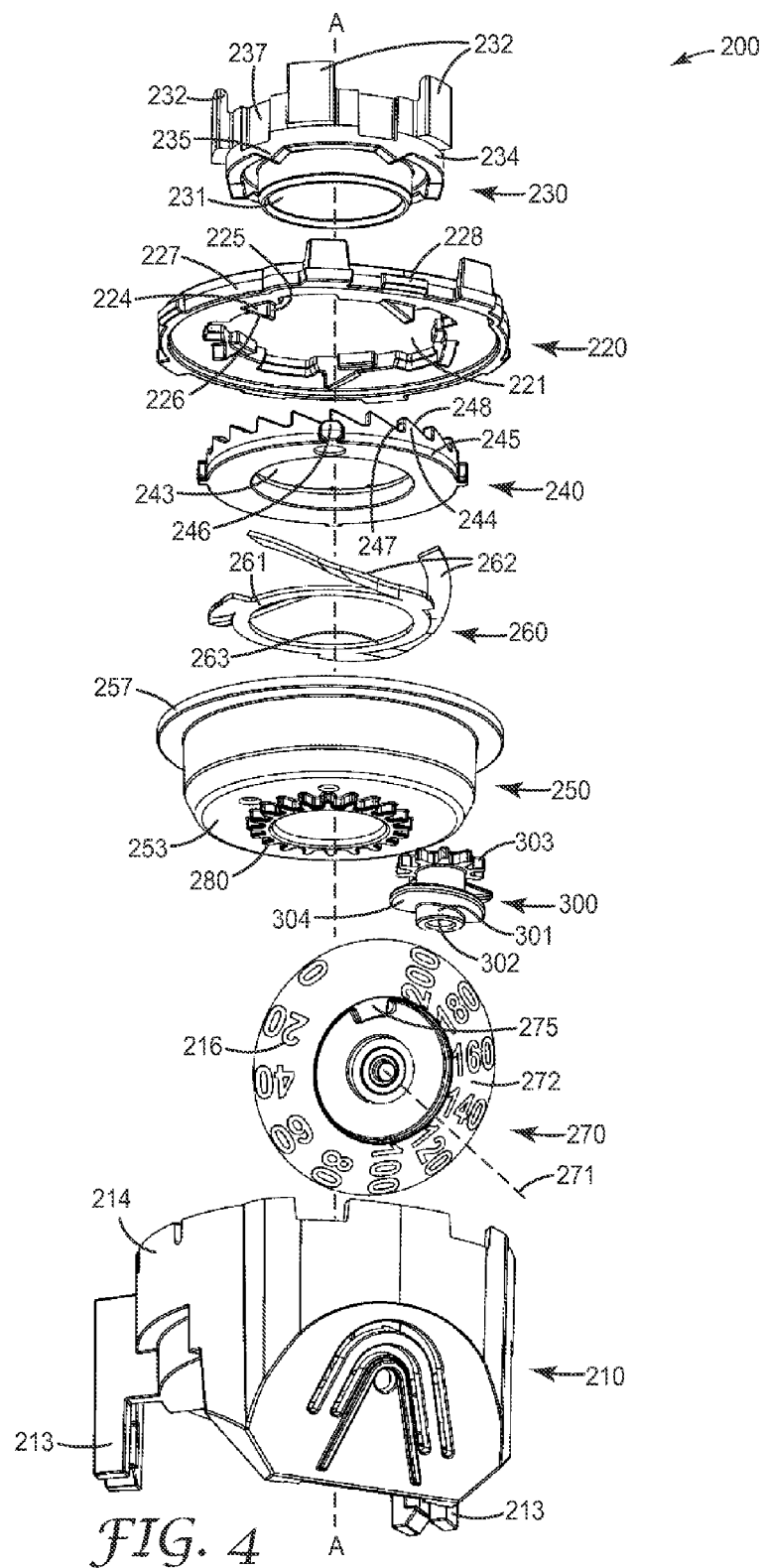
FIG. 4 represents another exploded view of the dose counter illustrated in FIG. 3 viewed from a different angle.
Figure 5B:
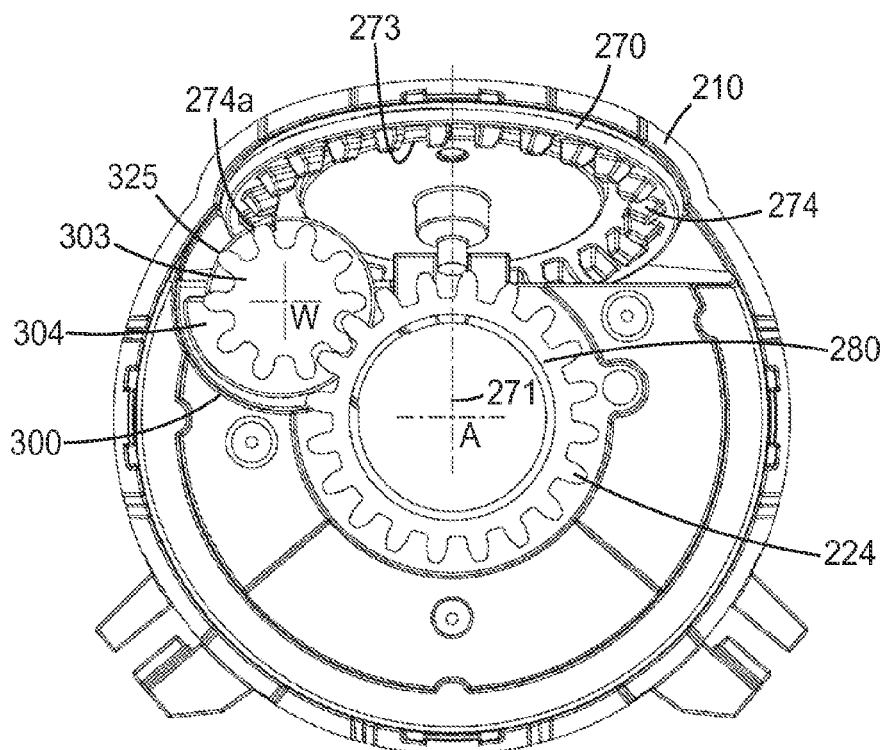
Figure 6A:
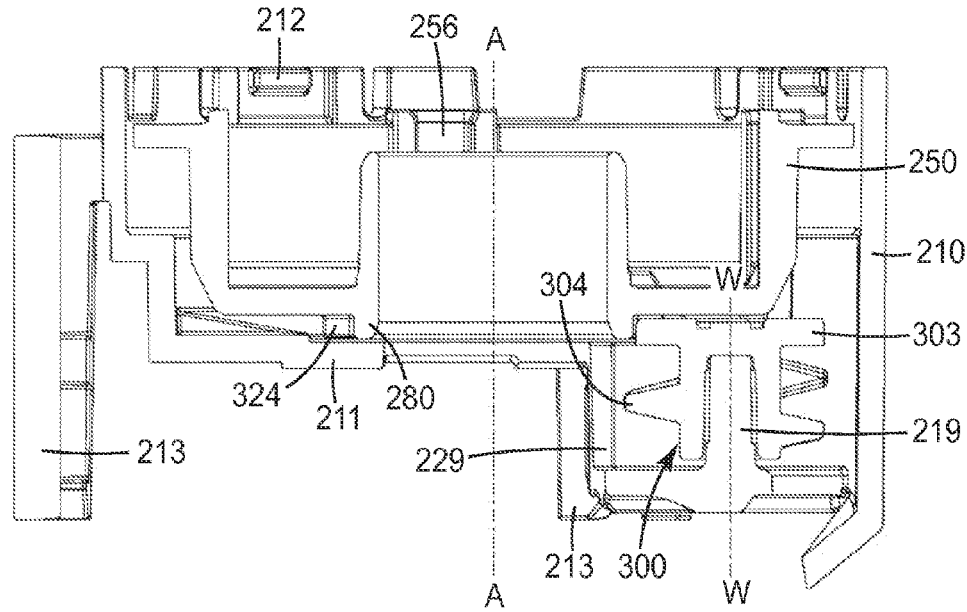
FIGS. 6a and 6b provide partial, vertical cross sections through the dose counter illustrated in FIG. 3, showing the first axis and worm axis (FIG. 6a), and the first and second axes (FIG. 6b).
Figure 6B:
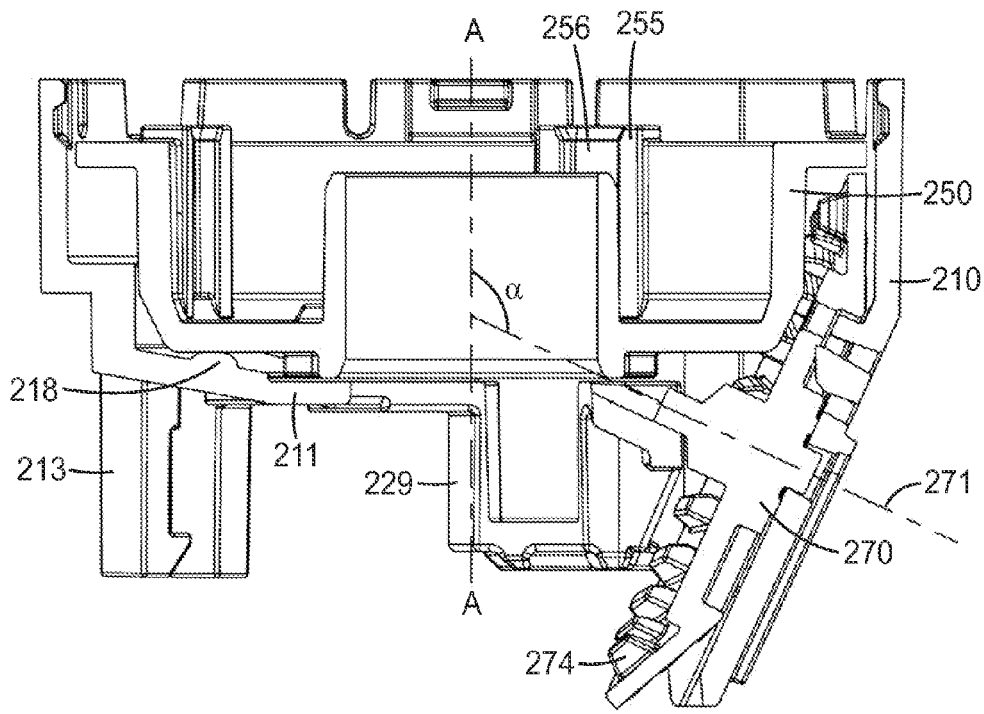

FIGS. 3 and 4 represent exploded views from two different directions of a dose counter (200) orientated in respect to their position about the first axis (A) (the actuation axis). Besides the lid (220) and housing (210), the dose counter (200) comprises an indicator member (270) and a worm (300). When the dose counter is used in conjunction with an inhaler, such as the pressurized metered dose inhaler illustrated in FIG. 1, the dose counter may be mounted within the actuator such that the indicator member (270) faces towards the back so that indicia (216) provided on an indicium- or indicia-bearing surface (272) of the indicator member can be seen through the window (30) provided in the actuator. The indicator member (270) is constructed and arranged to undergo predetermined count-indicating motion when one or more doses are dispensed. It can be recognized that the indicator member (270) is rotatable about a second axis (271), wherein the second axis is disposed at an obtuse angle with respect to the first axis (A). The latter is best seen in FIG. 6b showing a partial, vertical cross section through the exemplary dose counter showing the first and second axes (A and 271) and the obtuse angle ($\alpha$). (The worm is not shown in FIG. 6b.) Viewing FIG. 6b (which shows the indicator member from the side) in conjunction with FIG. 5b (which shows the indicator member from the top) it will recognized that the second axis (271) intersects the first axis (A). In the illustrated, exemplary embodiment the obtuse angle is about 115 degrees.

As indicated above, in favoured embodiments the first and second axes are disposed at an obtuse angle of 145 degrees or less relative to each other, in particular 135 degrees or less relative to each other, more particularly 125 degrees or less relative to each other, most particularly 120 degrees or less relative to each other. The first and second axes are favourably disposed at an obtuse angle of 95 degrees or greater relative to each other, more favourably 100 degrees or greater relative to each other, even more favourably 105 degrees or greater relative to each other, most favourably 110 degrees or greater relative to each other. As indicated above, desirably the first and second axes intersect.

As indicated above, an indicator member desirably comprises a indicium- or indicia-bearing surface, for e.g. indicating how many doses or how much medicament is contained in the container and/or how many doses or how much medicament has been dispensed from the container and/or that there is medicament still contained in the container that may be dispensed from the container and/or the container is or is considered empty. Indicia may be in the form of a sequence of numbers either increasing in value or decreasing in value around the indicator member. Alternatively or additionally, if desired, indicia may be colours. For example, a change of colour, for example from green to red, may be used to indicate the relative level of the medicament remaining in the container. In such cases, an indication of the medicament status is sufficient; however the dose counter is still generally required to count each dose dispensed. Other indicia will be known to a person skilled in the art. To favourably allow the provision of a relatively large area for the provision of an indicium or indicia and thus facilitate ease in viewing, an indicium- or indicia-bearing surface of the indicator member is desirably a conical or frustoconical surface relative to the second axis.

In the illustrated exemplary embodiments the indicator member (270) has a series of indicia (216) disposed about the external frustoconical, indicia-bearing surface (272) in the form of numerals 200 in 20's down to zero (see e.g. FIG. 4). The frustoconical, indicia-bearing surface (272) is arranged such that the portion of the surface carrying the indicia (216) is visible through a window (30) of an actuator (cf. FIG. 1) and is orientated vertically so that the indicia may be viewed square on.

Figure 8:
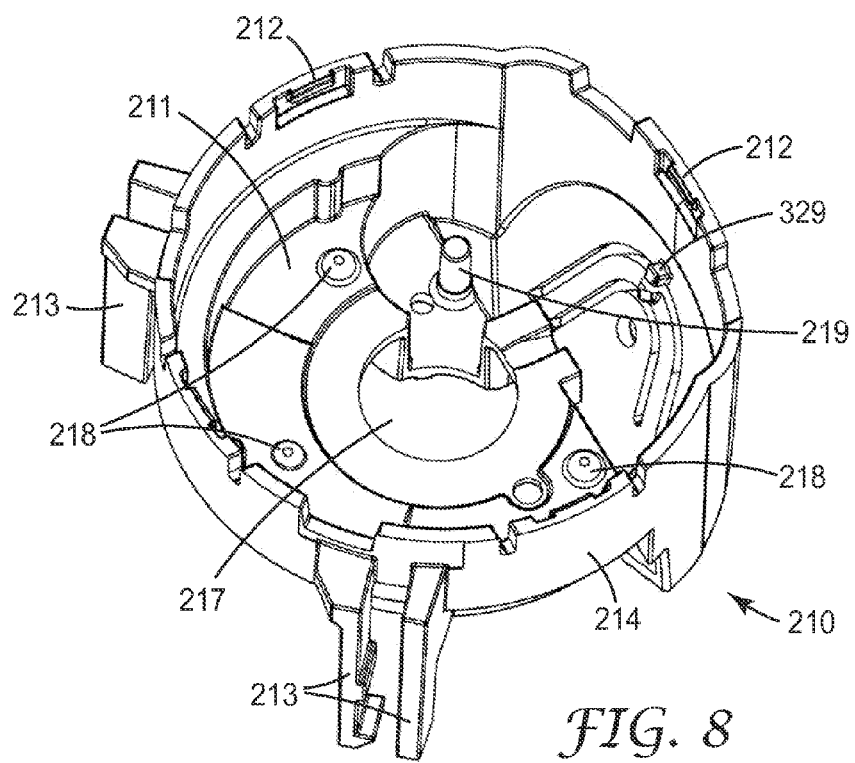
FIG. 8 shows inside of the lower portion of the housing of the dose counter illustrated in FIG. 3.

Referring to FIGS. 3 and 4 it can be seen that the worm (300) typically includes a worm thread (304) and a central shaft (301). The worm is configured and arranged to drive the indicator member (270) as discussed in more detailed below. The worm is rotatable about a worm axis, labelled "W" in FIG. 3. Referring to FIG. 8 showing the inside of the housing (210), in the illustrated embodiment a blind central hole (302) of the worm (visible in e.g. FIG. 4) engages a vertical post (219) extending from the floor of the housing (210), such that the worm is free to rotate about its vertical axis (W). FIG. 6a shows how the worm is mounted within the housing on the post (219) that extends from a lower section (229) of the housing. Referring to FIGS. 6a and 6b providing partial, vertical cross sections through the dose counter (FIG. 6a with the worm but without the indicator member and FIG. 6b without the worm but with the indicator member), it can be seen that the worm axis (W) and the second axis (271) are not disposed in a perpendicular alignment to each other. Referring to FIG. 5b which provides a cut away view from above, it can be seen that the worm axis (W) and second axis (271) do not intersect.

In general the worm and second axes are not co-axial, since the worm is arranged to drive the indicator member. While the worm and second axes could be parallel, for favourable functionality and optimal use of space, desirably they are not parallel to one another.

As mentioned above, favourably the worm axis and first axis are not coaxial. Also it is desired that the worm axis does not intersect the first axis.

It is favourable to arrange the counter such that the worm axis is disposed from an angle of 180 degrees ("exact parallel alignment") to (and including) an angle of 160 degrees with respect to the first axis. It is more favourable (e.g. due to enhanced simplicity in design, assembly and manufacturing as well as operation) to dispose the worm axis in parallel alignment to the first axis. In regard to such more favoured embodiments it should be appreciated that because of e.g. tolerances in manufacturing and assembly, the worm axis in a working, mass-produced dose counter may be deposited plus or minus three degrees from an exact parallel alignment to the first axis ("essentially parallel alignment"), and thus for this reason it will be understood that the general phrase "worm axis is disposed in parallel alignment to the first axis" includes "exactly parallel" as well as "essentially parallel" alignments.

In the illustrated exemplary embodiments, the worm axis (W) is parallel to the first axis (A), which will be appreciated from a study of any one of FIGS. 3 to 6a or FIG. 8. In FIG. 8, it can be seen the vertical post (219) is positioned off-centre from the central hole (217) of the housing.

Desirably the indicator member comprises a region for interaction with the worm, wherein the region of the indicator member and the worm are configured and arranged such that at least one portion of the region of the indicator member meshes with at least one portion of the thread of the worm. More desirably such a region of the indicator member is configured and arranged as a worm wheel.

Referring to the illustrated embodiment (see e.g. FIGS. 3 and 5b) it can be seen that the inner surface (273) of the indicator member (270), i.e. the surface opposite the indicia-bearing surface (272) of the indicator member, includes protruding members (274) extending outwardly from the inner surface and arranged in a circular pattern forming a worm wheel. In the illustrated embodiment, the protruding members are in the form of spokes (274) that are oblong shaped with chamfered edges. The spokes are desirably spaced apart sufficiently to allow the thread to pass between them and engage the lower surface (321a) of a higher spoke (274a) and the upper surface (322b) of a lower spoke (274b) (see FIG. 7e). As can be appreciated from FIG. 7d, it is desirable to provide sufficient leeway to allow for different orientations of a spoke (274) during its transit as it pasts the worm (300) and to allow for interaction of different portions of the thread and spokes during transit.

Protruding members may be any form suitable for engagement with a thread of a worm, e.g. in the form of spokes, ribs, posts, lugs, knobs, pins and the like. Depending on the particular configuration and arrangement of a dose counter, it will be appreciated that a worm wheel may be formed of protruding members extending radially outwardly. Worm wheels may be an integral component of an indicator member (e.g. as in the illustrated exemplary dose counter) or alternatively worm wheels may be a separate component appropriately directly affixed or indirectly coupled to an indicator member.

In the illustrated, exemplary dose counter, the thread (304) of the worm (300) rises generally upwards when viewed from the top of the worm (300) and extends for greater than 360 degrees (more than one turn). A vertical overlap of the worm thread advantageously allows for permanent engagement with at least one protruding member (274) on the indicator member (270), because for at least a short part of the turn, two protruding members are engaged simultaneously. Such engagement is advantageous for a number of reasons including minimizing or preventing the indicator member (270) from rotating independently of a count and enhancing the precision of entry of an arriving protruding member due to secure (still engaged) positioning of a departing protruding member.

Accordingly, in general it is advantageous to provide a worm thread that extends greater than 360 degrees (i.e. has more than one turn), more particularly extends greater than 365 degrees, and most particularly extends greater than 375 degrees. If desired, the worm thread may have more than two turns, however it has been found advantageous for functionality and for ease of manufacturing to have two turns or less, in particular while having more than one turn.

Relative to the angle between the worm axis and second axis, the cross-sectional radius of the worm from the worm axis to the outer edge of the worm flight desirably generally increases along the worm axis. This may be accomplished by generally increasing the cross-sectional diameter of the worm shaft along the worm axis or by generally increasing the cross-sectional width of the worm thread perpendicular to the worm axis along the worm axis or by both.

Referring to FIG. 7 (in particular FIGS. 7a, 7d, and 7g) it can be seen that in the exemplary embodiment the cross-sectional width of the worm thread (304) perpendicular to the worm axis (W) generally increases along the worm axis. In particular the outer edge (305) has a trajectory in which the perpendicular distance from the worm axis (W) increases with increasing angle of turn and as the thread (304) rises towards the top of the worm (300). Accordingly the cross-sectional radius of the worm from the worm axis to the outer edge of the worm flight generally increases along the worm axis. This facilitates the meshing of one or more protruding members (274) on the indicator member (270) with portions of the thread (304) while the indicator member (270) is been driven by the worm (300), although the second and worm axes (271, W) are not in a perpendicular alignment relative to each other. As can be appreciated from FIG. 7a, in the illustrated, exemplary embodiment the second axis is favourably disposed at an obtuse angle (β) with the respect to the worm axis.

The trajectory/rate of increase of the outer edge of the flight may be an arc or linear with vertical distance. Generally an arc is advantageous to allow for more precise tracking of protruding members associated with an indicator member; however in practice a linear rate of extension has also been found suitably accurate to provide sufficient tracking, both advantageously minimizing or preventing undesired wobbling of an indicator member due to excessive clearance between engaging portions/surfaces of the worm and indicator member. In the illustrated exemplary dose counters, generally each complete (360 degree) turn of the worm (300) provides 15 degrees of rotation of the indicator member (270). In the illustrated exemplary dose counters, upon one count the worm rotates about 36 degrees and drives the indicator member about 1.5 degrees.

Desirably worms are configured and arranged to undergo a predetermined rotational motion each time a dose is dispensed. Such rotational motion then drives the indicator member so that it achieves its predetermined count-indicating motion when one or more doses are dispensed. The indicator member may undergo a predetermined count-indicating motion each time a dose is dispensed or alternatively the indicator member undergo a predetermined count-indicating motion after a plurality of doses have been dispensed, for example after every five or every ten doses. Dose counters are desirably configured and arranged to induce the worm's predetermined rotational motion in coordination with reciprocal movement of the reciprocal actuation means (e.g. a valve) and the container.

Exemplary dose counters illustrated in FIGS. 2 and 3 favourably include, in addition to the aforementioned components, a counter member (240), a count-transferring member (250), an indexing member (230), and a spring (260). As can be taken from e.g. FIGS. 3 and 4, all of these components are oriented about the first axis (A). Exemplary dose counters also comprise a gear (303) provided coaxially (rotatable along the worm axis (W)) to the worm (300). In the illustrated embodiments the gear (303) is an integral portion formed at the top end of the central shaft (301) of the worm (300); however in alternative embodiments, the gear may be a separate component appropriately directly affixed or indirectly coupled to the worm.

In the illustrated embodiments the counter member (240) as well as the count-transferring member (250) are desirably constructed and arranged to undergo predetermined counting or count-transferring motions, respectively, each time a dose is dispensed. Generally the count member (240) induces (rotational or essentially rotational) movement of the count-transferring member (250), and the count-transferring member induces rotational movement of the worm (300) which in turn induces rotational movement of the indicator member (270).

The counter member (240) is provided with at least four regions of interaction: a first with the count-transferring member; a second with ratchet member(s) provided on the lid; a third with the indexing member (in particular with saw-tooth protrusions thereof); and a fourth again with the ratchet member(s). In particular, the counter member is provided with two rings of upstanding teeth, an inner ring of teeth (241) and an outer ring of teeth (244), around a central cylinder (242) with a central hole (243). The outer ring of teeth (244) is disposed for interaction and engagement with ratchet members (224) provided on the bottom surface of the lid (220). The teeth of the outer teeth ring (244) comprise two regions for interaction: one region is a vertical surface (247) (i.e. the counter member's second region of interaction); the other region is an inclined surface (248) (i.e. the counter member's fourth region of interaction). An inner ring of teeth (241) is arranged for interaction and engagement with the saw-tooth protrusions (235) on the indexing member (230) (i.e. the counter member's third region of interaction) during the outward stroke of the indexing member, and favourably also during the return stroke of the indexing member of the illustrated embodiment. A circumferential perimeter (245) of the counter member (240) has a plurality of circumferentially equally spaced protrusions (246) extending outwards. The protrusions (246), representing the counter member's first region of interaction, are arranged for engagement and interaction with the count-transferring member (250).

The count-transferring member (250) is generally in the form of inner (251) and outer (252) coaxial cylinders, joined by an annular base (253). A plurality of bearing surfaces (218) are disposed on a shelf (211) (see FIG. 8) in the housing (210), providing a low friction surface on which the count-transferring member rests and rotates. Vertical movement of the count-transferring member (250) is favourably limited or essentially prevented by inter alia how it is held within the housing of the dose counter. FIG. 6*a* shows how the count-transferring member (250) is mounted within the housing (210).

It will be appreciated that the counter member and the count-transferring member may be, independently, provided in various forms including rings, cylinders, disks or cones. It will also be appreciated that the two members may be nested.

The inner cylinder (251) of the count-transferring member (250) has a diameter such that it slides axially inside the central cylinder (242) of the counter member (240). The outer cylinder (252) has a thin outer cylindrical surface (257). The outer circumferential perimeter (245) of the counter member (240) is slightly smaller in diameter than the internal surface (254) of the outer cylinder (252) of the count-transferring member (250), thus allowing axial (vertical) movement of the counter member (240) relative to the count-transferring member (250) and rotational movement of the counter member relative to the housing (210).

The count-transferring member (250) includes a region for interaction and engagement with the counter member (240). In particular the count-indicating member includes at least one channel (256) including a pair of inwardly facing ribs (255) on either side of a channel, and in particular four channels. The channels are arranged for engagement and interaction with the corresponding protrusions (246) of the counter member (240). The protrusions (246) extend outwardly, and engage the channels (256) of the count-transferring member (250). Desirably, the protrusions (246) are a good fit in the channels (256) with little clearance. In the exemplary embodiments the channels are generally vertical, parallel to the first axis (A), and rotational or helical (vertical and rotational) movements of the count member will generally induce rotational movement of the count-transferring member. In such embodiments the count member and count-transferring member will generally rotate in tandem. In other alternative embodiments (not shown) the channels may be inclined, i.e. angled relative to the first axis (A). As described in detail in our co-pending application (GB application No. 09 20499.1, filed Nov. 23, 2009 (Stuart)) in such embodiments the count member and the count-transferring member, although always completing a count in tandem, do not always move in tandem over the operation of the dose counter; this feature provides inter alia the benefit of releasing stiction between the components and the housing by directing the force applied by the patient directly (without spring compensation) especially during the very beginning of the dose counter operation.

The count-transferring member (250) includes a second region for interaction with the worm (300). In particular the inner cylinder (251) of the count-transferring member (250) extends at its lower end (i.e. below the annular base (253)) into a horizontal and coaxial gear (280), which is thus rotatable about the first axis (A) (see e.g. FIG. 4). Here the gear (280) is an integral portion of the count-transferring member; however in alternative embodiments the gear may be a separate component suitably directly affixed or indirectly coupled to the count-transferring member. The gear (280) of the count-transferring member ("first gear") interacts and engages with the gear (303) coaxially affixed to the top end of worm (300) ("second gear"), so that rotation of the count-transferring member (250) is translated via the first and second gears (280, 303) into rotation of the worm (300). The rotation of the worm (300) in turn drives the indicator member (270) via interaction and engagement of the worm thread/flight and protruding members (274).

Figure 5A:
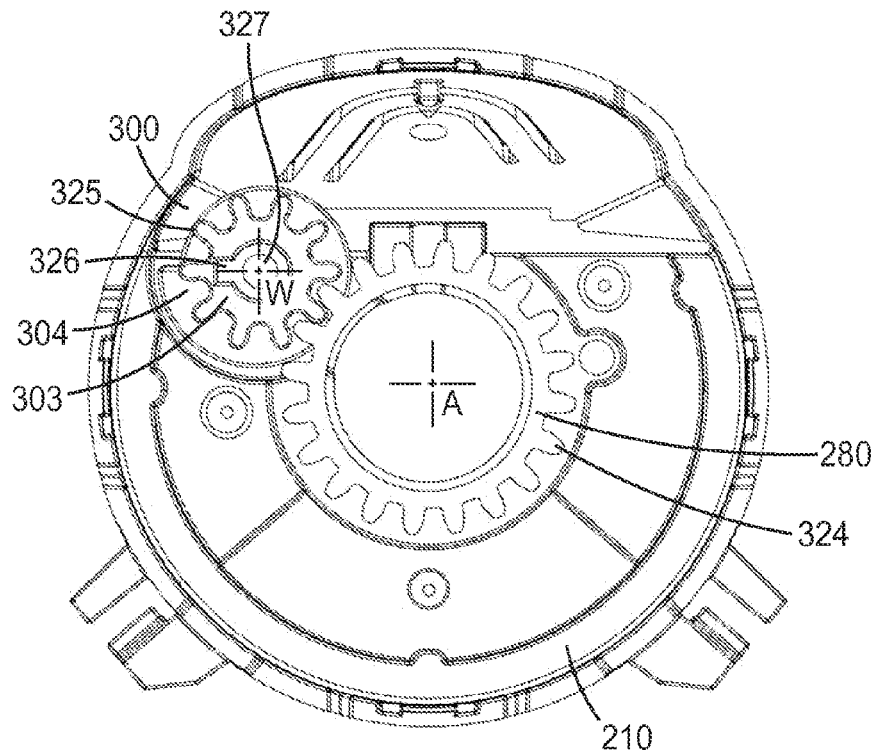
FIGS. 5a and 5b provide cut away views from above the dose counter illustrated in FIG. 3 without and with the indicator member, respectively.

FIG. 5*a* shows a cut away isometric view vertically downwards into the housing (210) of the dose counter, showing the gear (280) of the count-transferring member (the member otherwise not being shown) and the gear (303) of the worm (300), but not showing the indicator member. It can be seen that teeth (324) of the first gear (280) engage teeth (325) of the second gear (303). The thread (304) of the worm is visible. Additionally, end-on views of the first axis (A) of the dose counter (200) and the worm axis (W) of the worm (300) are shown by intersection of crossed dashed lines. It can be seen that on top of the gear (303) of the worm, there is a keyhole-shaped recess (326) with a protruding flat cylinder (327) extending axially from the shaft, intended to allow orientation of the worm during assembly.

FIG. 5*b* shows a different cut away isometric view vertically downwards into the housing (210) of the dose counter, showing inter alia teeth (324) of the first gear (280) engaging teeth (325) of the second gear (303) and a portion of the worm thread (304) engaging at least one (274*a*) of the protruding members (274) on the internal surface (273) of the indicator member (270). The axis (271) of the indicator member (270) is shown to intersect the first axis (A); although in this view the angle between the two axes in the vertical plane is not visible. During operation of the illustrated dose counter, relative to this view, the gear (280) turns clockwise, the gear (303) turns anticlockwise, and the indicator member (270) turns clockwise.

The lid (220) is generally annular with a central circular hole (221). The hole has a plurality of circumferentially equally spaced radial hole extensions (222) of slightly greater radius and a plurality of circumferentially equally spaced small radially inward protrusions (223). Around the central hole (221) on the bottom surface of the lid (220) are a plurality of ratchet members (224), comprising two regions for engagement and interaction with the counter member (240); one region is a vertical surface (225) and the other region is an inclined surface (226). Disposed around the outer circumferential edge (227) of the lid (220) are a plurality of protrusions (228) that provide a means of correctly orientating and securing the lid (220) to the housing (210).

The indexing member (230) is shaped generally like a cylindrical cap with a central hole (231). The indexing member (230) has a plurality of peripheral castellations (232) that are designed to pass through the radial hole extensions (222) of the lid (220). The indexing member (230) also has a plurality of peripheral grooves (233) designed to accommodate the inward protrusions (223) of the lid (220). The combination of these features allows for axial (vertical) movement of the indexing member relative to the lid, while securing the indexing member within the dose counter. On a bottom circumferential edge (234) of the indexing member (230) a plurality of circumferentially equally spaced saw-tooth projections (235) are provided for interaction with the inner ring of teeth (241) on the counter member (240). The upper portion of the indexing member includes a castellation-bearing wall (237) and a circumferential ridge (236) that defines a sunken, cylindrical space.

The spring (260) that provides a biasing means can be in the form of an annular leaf spring. The leaf spring (260) has an annular ring (261) with a plurality of spring elements (262) or leaves extending generally helically (coaxially with the ring) from radial projections on the circumference of the ring. The inner circumferential edge (263) of the leaf spring (260) is slightly larger in diameter than the outer surface (258) of the inner cylinder (251) of the count-transferring member (250) such that the bottom surface of the leaf spring (260) engages with the top surface (259) of the annular base (253) of the count-transferring member (250). The spring elements (262) are biased upwardly from the leaf spring (260) such that they engage with the bottom surface of the counter member (240). The leaf spring (260) thus biases the counter member (240) axially away from the annular base (253) of the count-transferring member (250) and towards the saw-tooth projections (235) on the indexing member (230) and towards the ratchet members (224). Thus the outer ring of teeth (244) is biased towards the ratchet members (224) and the inner ring of teeth (241) is biased towards the saw-tooth projections (235). The pair of such that engage at any stage of operation is determined by the relative rotational positions of the indexing member (230) and the counter member (240).

The dose counter housing (210) has a generally cylindrical body with a plurality of clip features (212) to engage with the protrusions (228) of the lid (220) to provide a means of securing the lid (220) to the housing (210). Two forward legs (213) are provided for engagement of the dose counter (200) with an interior surface of an actuator (e.g. an actuator of the type illustrated in FIG. 1). As mentioned above, the sidewall (214) of the housing of the embodiment shown in FIG. 3 is made of a transparent material.

FIG. 8 shows a view into the housing of the dose counter (200) shown in FIG. 3. The dose counter (200) may be assembled by inserting the indicator member (270) into the tapering housing section of the housing (210). The worm (300) is dropped onto the vertical post (219). The count-transferring member (250) is then inserted and seated on a shelf (211) of the housing (210). The count-transferring member is located above the indicator member (270) and the gear (280) of the counter-transferring member engages the gear (303) of the worm (300). The leaf spring (260), counter member (240) and indexing member (230) can then be assembled in order over the count-transferring member (250), and finally the lid (220) can be fitted about the peripheral castellations (232) of the indexing member (230). As described above, the lid (220) is snap-fit engaged with the dose counter housing (210) by engagement of the protrusions (228) and associated clip features (212). The lid (220) and housing (210) may be otherwise connected together, such as by press fit connections, or may be ultrasonically or otherwise welded together.

Exemplary dose counters illustrated in FIGS. 2 and 3 are particularly suitable for use in an actuator of a pressurized metered dose inhaler. Referring to FIGS. 2 and 3 in conjunction with FIG. 1, in particular the outlined profile form of the dose counter shown in FIG. 1 and the corresponding profile form shown in FIG. 2, it will be recognized that dose counters (200) of FIGS. 2 and 3 may be suitably mounted within the interior of the actuator (20) generally positioned beneath the container (16) near and around the nozzle block (21) of the actuator. Further it can be recognized that the castellations (232) of the indexing member (230) may surround the ferrule (18). The ferrule may then be located within the sunken, cylindrical area defined within the castellation bearing wall (237) (see FIG. 2) and circumferential ridge (236). Although not readily apparent from FIG. 1, the legs (213; one visible in FIG. 2) of the dose counter (200) may suitably engage with the bottom floor (32) of the actuator (20).

The operation of a dose counter such as one illustrated in FIG. 2 or FIG. 3 with a pressurized metered dose inhaler such as that shown in FIG. 1 can be described in the following—in two parts (1) the movements of the counter member and count-transferring member and (2) the movements of the worm and indicator member:

At the rest position of the dose counter (200), the vertical surfaces (225) of the ratchet members (224) disposed on the bottom surface of the lid (220) are engaged with the vertical surfaces (247) of the outer ring of teeth (244) on the counter member (240). Also, the protrusions (246) on the outer perimeter of the counter member (240) are engaged with the channels (256) on the interior side of the outer cylinder (252) of the count-transferring member (250). The leaf spring (260) additionally urges the counter member to its uppermost vertical position. Engagement of the aforementioned regions together with the bias provided by the dose counter spring prevents the counter member and count-transferring member from undergoing any rotational movement during storage and handling. The ferrule (18) may be resting on the circumferential ridge (236) of the indexing member (230) or the ferrule (18) may rest clear of the indexing member (230). The saw tooth projections (235) of the indexing member may be resting on the inner ring teeth (241) of the counter member (240).

As the user presses down on the aerosol container (16) to initiate actuation of the inhaler (5), the downward vertical movement of the aerosol container towards the nozzle block (21) causes the ferrule (18) to engage (if it has not already done so) and then push down on the circumferential ridge (236) of the indexing member (230), thus causing a downward vertical movement of the indexing member and thus initiating the outward stroke of the indexing member. Then, the saw-tooth projections (235) of the indexing member (230) engage (if they have not already done so) and push down on the inner ring teeth (241) of the counter member (240). These regions of interaction are favourably configured to have opposing angular surfaces and are arranged such that when force is applied, the saw-tooth projections (235) and inner teeth ring (241) urge the counter member (240) to rotate. However, at first, the ratchet members (224) and the outer teeth ring (244) (i.e. the vertical surfaces of each (225 and 247, respectively)) are still engaged, limiting any rotational movement of the counter member (240). Hence the applied force induces the indexing member (230) to move vertically downwards, and the indexing member in turn induces the counter member (240) to move in a downwards, vertical or essentially vertical direction against the opposing force from the leaf spring biasing element (260). As the counter member (240) moves vertically or essentially vertically downwards, the counter member protrusions (246) also move correspondingly vertically downwardly in the channels (256) of the count-transferring member (250).

As the downward force from the user on the container continues, the counter member (240) will continue to move (essentially) vertically downwards until the ratchet member (224) disengages from the counter member (240). However if the user relieves his force on the container before disengagement from the ratchet member, the counter member (240) will return to the first rest position, and no dose count will be recorded.

While the patient continues to press down on the aerosol container (16), the indexing member (230) and counter member (240) continue to move downwardly until such time as the counter member's outer teeth (244) disengage from the ratchet members (224) (in particular until the vertical surfaces of each (247 and 225, respectively) disengage). Upon disengagement a dose count is committed to and is therefore non-reversible. Furthermore, upon disengagement the counter member is free to rotate and will rotate under the force of the bias. If applicable (i.e. if the user continues to press down on the container to complete actuation of the inhaler), the counter member will also continue to move vertically downward under the force of the user via the indexing member. As mentioned above, the regions of interaction of the indexing member (230) and the counter member (240) include the saw-tooth projections (235) of the indexing member (230) and the inner teeth ring (241) of the counter member (240). The angular surfaces of said regions (235 and 241) are configured and arranged such that when force is applied by a bias, e.g. the leaf spring (260), the regions are urged vertically towards each other and since the indexing member (230) cannot rotate, the interaction between the saw-tooth projections (235) and inner teeth ring (241) now causes the counter member (240) to rotate. The count-transferring member rotates essentially in tandem with the rotational movement of the counter member. Once again, if applicable the counter member may simultaneously move vertically, so that the movement in total is an essentially helical movement; however it is generally the rotational component that induces the rotational movement of the count-transferring member.

Due to inter alia engineering tolerances it is normally difficult to have the points of no return of a dispensing cycle and a dose counting cycle synchronized, and thus generally the point of no return for a dose counter is typically purposely set to be earlier than that of the dispenser, so that there is normally a tendency to over-count rather than under-count. Accordingly typically after the point of no return for a dose counter, the user typically still needs to apply some more force on the container to cause actuation of the inhaler.

The patient will typically continue to apply force to the aerosol container (16) until a metered dose is released. Typically this will occur shortly after the disengagement described above, to ensure that the dose count has been committed to prior to releasing medicament and hence minimizing any potential to under-count administered doses. After the medicament has been released, the user may (and most often does) continue to apply force onto the aerosol container, thus inducing a continued outward stroke of the indexing member (230). This movement is however generally not necessary for the dose counter to complete its counting motion. During this movement, the counter member (240) can move vertically downwards until the protrusions (246) of the counter member reach the bottoms of the channels (256) of the count-transferring member (250).

When the user of the inhaler releases pressure on the aerosol container (16), the force on the indexing member is released and the valve ferrule (18) is biased upwards away from the indexing member by the spring (24) in the valve, so the indexing member is allowed to commence its return stroke. Moreover, the counter member (240) is urged, under the force of the leaf spring (260), vertically upwards towards the ratchet member (224), thereby moving the indexing member (230) vertically upwards. As the counter member continues to move vertically upwardly, the inclined surfaces (226) of the ratchet members (224) and the inclined surfaces (248) of the outer ring of teeth (244) of the counter member (240) engage. The two sets of inclined surfaces (226, 248) are configured and arranged such that as the counter member (240) undergoes a further vertically upward movement under the resultant force of the leaf spring (260), the engagement and sliding of said inclined surfaces of the counter member over the inclined surfaces of the fixed ratchet members (224)

induces further rotational movement of the counter member (240), which in turns induces a further rotational movement of the count-transferring member. The last rotational movement of the counter member allows for completion of its predetermined counting motion. As the counter member moves vertical upwards and rotates to complete its predetermined counting motion, the indexing member is continually moved vertically upwards and each saw-tooth projection (235) moves over a tooth of the inner set of teeth (241) when they are vertically clear to do so under the bias of the interaction between the two sets of inclined surfaces (226, 248). The indexing member (230), leaf spring (260) and counter member (240) return to a second rest position where each set of teeth (241, 244) of the counter member has been incremented by one tooth and the count-transferring member (250) has rotated an increment corresponding to one count (and where accordingly the first gear (280) associated with the count-transferring member (250) has also been incremented by one tooth).

The operation of the worm and indicator member is linked to the operation described above, in particular to the rotation of the count-transferring member via the first and second gears (280, 303).

The operation of the indexing member (230), the counter member (240) and the spring (260) of the dose counter (200) drives the count-transferring member (250) in rotational increments, which are in a clockwise direction when viewed from above. The first gear (280) of the count-transferring member (250) typically has 20 teeth (see e.g. FIG. 5a or b), and consequently it makes a complete rotation (which is clockwise) after 20 counts, where each tooth corresponds to a count of one dose. The second gear (303) of the worm (300) typically has 10 teeth (see e.g. FIG. 5a or b), and consequently it makes a complete rotation (which is anticlockwise) after 10 counts, where again each tooth corresponds to a count of one dose. The gear ratio of the first gear to the second gear is therefore 2 to 1 (20 to 10 teeth). The worms of each the illustrated exemplary dose counter moves 36° per count, rotating the indicator member about 1.5 degrees. The gear ratio of the worm's rotation to the indicator member's rotation is therefore 24 to 1 (36 degrees to 1.5 degrees). Relative to the orientation shown in FIG. 5, the worm turns anticlockwise and the indicator member turns clockwise.

FIG. 7a is a representation of a first rest position prior to a count and FIG. 7b is a representation of a second rest position after one single count, i.e. where the worm has rotated 36 degrees and the indicator member about 1.5 degrees. For ease in following the movement of indicator member protruding member labelled "274a" is hatched. In FIG. 7a, the (vertical face of the) upper terminating end (307) of the thread (304) can be seen (to the right), and a portion near this end is engaged with a protruding member (274z) of the indicator member. In the illustrated exemplary embodiment, the thread desirably turns approximately 367°, and the portion of the thread near to the other, lower, terminating end (306) of the thread is engaged with the protruding member (274a) following the protruding member (274z) engaged by the portion near the upper terminating end (307).

After the first and second gears have caused the worm to rotate 36 degrees upon one count, it can be appreciated from FIGS. 7a and 7b—that the upper portion/end (307) of the thread has moved out of the shown plane (back out of the paper), disengaging protruding member 274z, while the rotational movement of the lower portion of the thread has pushed the following protruding member (274a) upwards, causing the indicator member to rotate 1.5 degrees. As generally indicated in the illustration of the thread in FIG. 3, it can be desirable to provide some lead-in in the form of a top chamfer of the vertical face of the bottom (leading) end of the thread to ease the initial engagement of a portion of the thread with a protruding member.

Figure 7C:
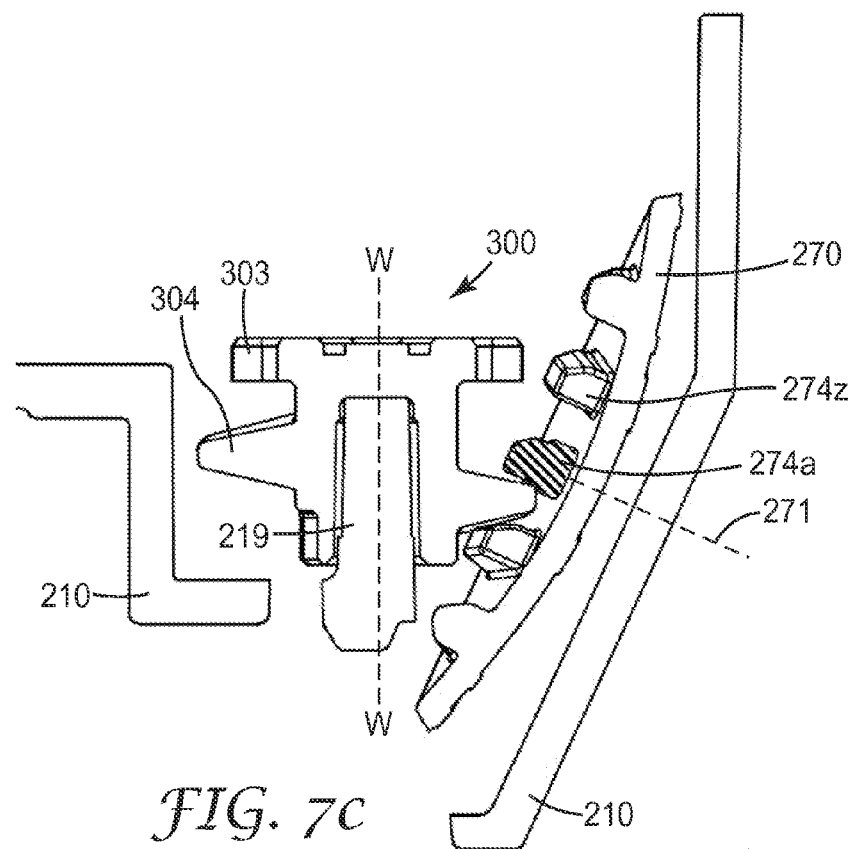
FIG. 7 (a) to (g) provide partial, vertical cross sections through the dose counter illustrated in FIG. 3 illustrating the underlying operation as well as the configuration and arrangement of the worm and the indicator member at selected angles of rotation of the worm.
Figure 7D:
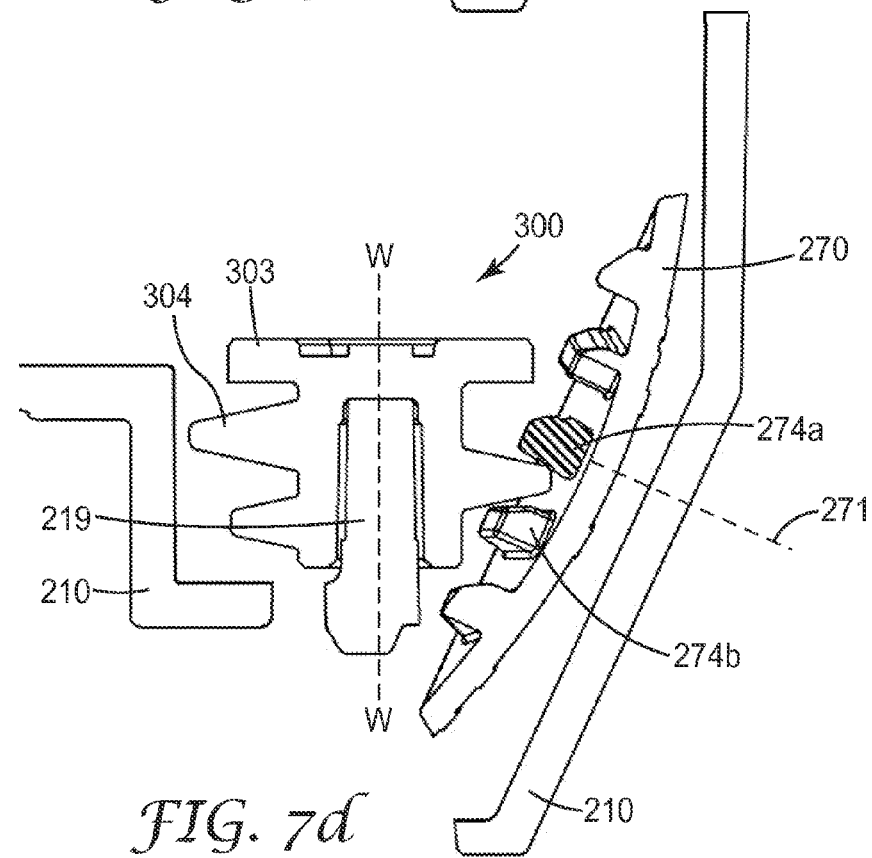
Figure 7E:
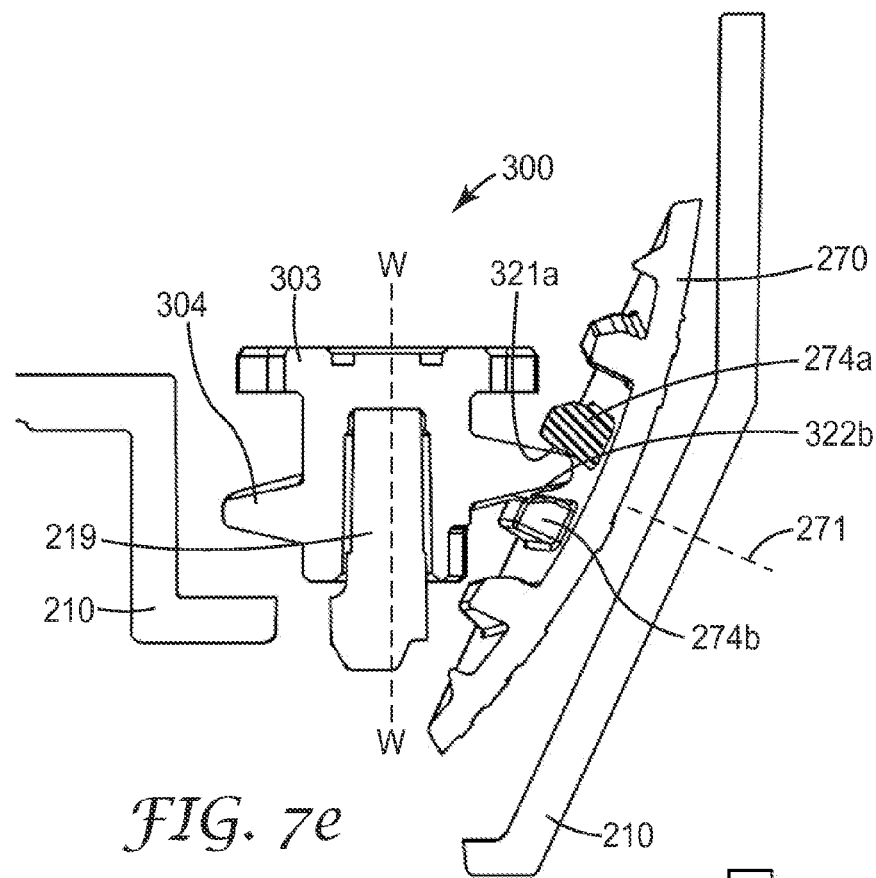
Figure 7F:
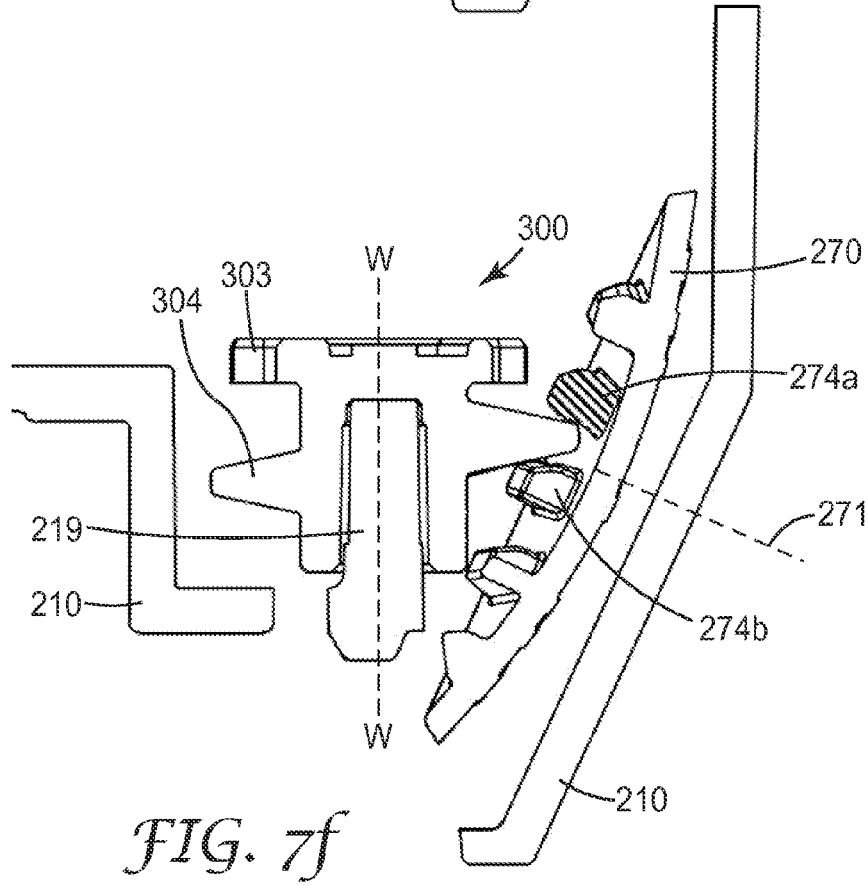
Figure 7G:
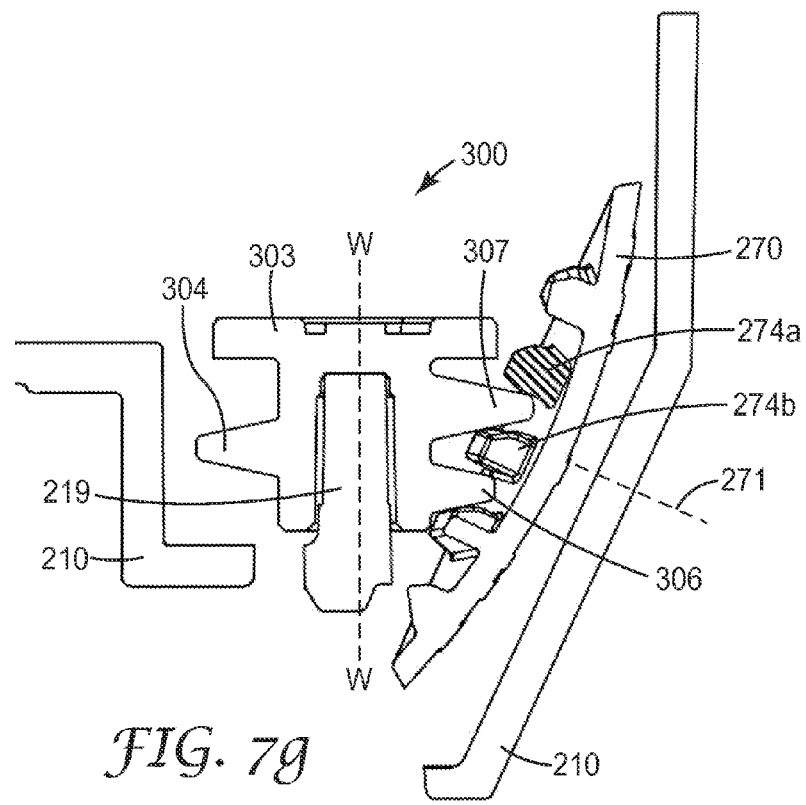

FIG. 7c illustrates the position when the worm has rotated 90 degrees (between two and three counts); FIG. 7d, 180 degrees (five counts); FIG. 7e, 270 degrees (between seven and eight counts); FIG. 7f, 350 degrees (almost ten counts); FIG. 7g, 360 degrees (tens counts).

As mentioned above, the second and worm axes are not in a perpendicular alignment relative to each other. The second axis may be favourably disposed at an obtuse angle with the respect to the worm axis, more favourably they are disposed at an obtuse angle of 95 degrees or greater relative to each other, even more favourably 100 degrees or greater relative to each other, yet even more favourably 105 degrees or greater relative to each other, most favourably 110 degrees or greater relative to each other. Generally for ease in operational engagement of the worm and the indicator member, the second and worm axes are favourably disposed at an obtuse angle of 145 degrees or less relative to each other, more favourably 135 degrees or less relative to each other, even more favourably 125 degrees or less relative to each other, most favourably 120 degrees or less relative to each other.

Relative to the angle between the worm and second axes, it has been found advantageous to provide a worm in which the cross-sectional radius of the worm from the worm axis to the outer edge of the worm flight generally increases along the worm axis. This facilitates inter alia the meshing of one or more protruding members on the indicator member with portions of the thread of the worm, and generally the larger the angle between the worm axis and the second axis, the steeper the increase of the aforementioned cross-sectional radius of the worm. It is further beneficial to desirably arrange the configuration and/or the positioning of the worm (in particular the thread thereof) and/or of the protruding members of the indicator member, so that the worm thread provides a near-tangential (relative to the second axis) torque against the protruding member(s). In order to further facilitate efficient and effective engagement between the thread and the protruding member or members, and/or for ease of moulding of the worm, it has been found advantageous to provide the thread of the worm in five sections differing in slope, in particular the sections bordering the two ends are generally horizontal, connected to two generally rising sections with a central generally horizontal section.

As the worm (300) rotates through 90 degrees (FIG. 7c), a rising section of the thread carries the protruding member (274a) upwards, taking the load as it rotates on its post (219). After five counts, the worm (300) has rotated 180 degrees from the position of FIG. 7a to the position shown in FIG. 7d, and it has brought the protruding member (274a) to its lateral extreme (i.e. to an extreme position to the left in FIG. 5b) where the protruding member is now carried by a central generally horizontal portion of the thread. After the worm (300) has rotated 270 degrees to the position shown in FIG. 7e, the protruding member (274a) being carried by a second rising section has been driven further upwardly and the indicator member has turned 11.25 degrees corresponding to midway between seven and eight counts. After the worm (300) has rotated 350 degrees to the position shown in FIG. 7f, the protruding member is carried by the upper generally horizontal portion of the thread. Also at this position there is only one protruding member (274a) engaged by the thread (304), but as the worm turns the next 10 degrees of rotation to complete 360 degrees of rotation (corresponding to 10 counts) to reach the position shown in FIG. 7g, the lower end, i.e. a portion thereof, of the thread engages the next following protruding member (274*b*). The previous protruding member (274*a*) is still engaged by a portion near the upper end of the thread. The position shown in FIG. 7*g* is equivalent to that shown in FIG. 7*a*, except that the indicator member has been rotated 15 degrees and thus a different pair of protruding members is engaged (274*a* and 274*b* instead of 274*z* and 274*a*).

In the illustrated exemplary dose counters, to avoid the indicator member counting beyond its given 200 counts and with continued use advancing beyond zero, a stop feature (275, shown in FIG. 4) on the indicator member comes into contact with a similar feature (329, shown in FIG. 8) on the inside of the housing. A similar stop feature is described in WO 2007/124406.

An alternative mechanism to stop an indicator member of a dose counter advancing beyond zero involves stalling or jamming the worm thread. This can be achieved by either having no protruding member(s) after the final driven protruding member (e.g. providing a gap of a width sufficient to extend to where at least the next protruding member would otherwise have been), or alternatively having a continuous surface rather than a gap between the final driven protruding member and the following protruding member that should not be picked up but would be picked up if the device were to continue. Where a gap is provided the worm flight would cease to drive the indicator member, which would remain in position with a display of zero. As the dose counter components further up the drive train are unaffected, actuation of the actuation means (e.g. valve) would still be possible. For the options in which either there is no gap between protruding members or a stop feature is used, the worm would jam into the indicator member and prevent any rotation. This would only jam the indicator member, worm, counter member and count-transferring member, whilst translation of the indexing member would be possible and thus actuation of the actuation means (e.g. valve) would still be possible.

The above described exemplary embodiment of a dose counter is described with reference to a pressurized metered dose inhaler. However it will be apparent to a person skilled in the art that the dose counter may be adapted for use with other actuators, dispensers or inhalers having a reciprocal actuation means, for example, nasal pressurized metered dose devices, dry powder inhalers or pump spray devices.

Dose counters are generally constructed from plastic components to keep the cost and weight of the dose counter to a minimum whilst maximising its strength and reliability. The most common exception to this is biasing elements (which as mentioned supra may be a spring, for example, a coil spring or a leaf spring) which may be formed from a plastic or metal, in particular steel or spring steel. If metal components are used, metallic materials that resist corrosion and/or oxidation are desirably chosen.

The invention claimed is:

1. A dose counter for use with an inhaler comprising a container for medicament equipped with a reciprocal actuation means to dispense a dose of medicament therefrom, said reciprocal actuation means operating along a first axis, the dose counter comprising:
    an indicator member rotatable about a second axis, wherein the indicator member is constructed and arranged to undergo predetermined count-indicating motion when one or more doses are dispensed and wherein the second axis is disposed at an obtuse angle with respect to the first axis, and
    a worm rotatable about a worm axis, wherein said worm is configured and arranged to drive said indicator member and wherein the worm axis and the second axis do not intersect and are not disposed in perpendicular alignment relative to each other.

2. A dose counter according to claim 1, wherein the first and second axes intersect.

3. A dose counter according to claim 1, wherein the worm axis and the first axis are not disposed in coaxial alignment relative to each other.

4. A dose counter according to claim 1, wherein the worm axis is disposed at an angle from 180 degrees to an angle of 160 degrees with respect to the first axis.

5. A dose counter according to claim 4, wherein the worm axis is in parallel alignment to the first axis.

6. A dose counter according to claim 1, wherein the indicator member comprises a region for interaction with the worm, and wherein said region of the indicator member and the worm are configured and arranged such that at least one portion of the said region of the indicator member meshes with at least one portion of a thread of the worm.

7. A dose counter according to claim 6, wherein said region of the indicator member is configured and arranged as a worm wheel.

8. A dose counter according to claim 1, wherein relative to the angle between the worm axis and second axis, the cross-sectional radius of the worm from the worm axis to the outer edge of a worm flight thread generally increases along the worm axis.

9. A dose counter according to claim 8, wherein the cross-sectional diameter of the worm shaft generally increases along the worm axis.

10. A dose counter according to claim 8, wherein the cross-sectional width of the worm thread perpendicular to the worm axis generally increases along the worm axis.

11. A dose counter according to claim 1, wherein the worm comprises a worm thread that has more than one turn.

12. A dose counter according to claim 1, wherein the worm comprises a worm thread that has less than two turns.

13. A dose counter according to claim 1, wherein the indicator member comprises a indicium- or indicia-bearing surface for indicating how many doses or how much medicament is contained in the container and/or how many doses or how much medicament has been dispensed from the container and/or that there is medicament still contained in the container that may be dispensed from the container and/or the container is or is considered empty.

14. A dose counter according to claim 13, wherein said bearing surface is a conical or frustoconical surface relative to the second axis.

15. A dose counter according to claim 1, wherein the first and second axes are disposed at an obtuse angle of 95 degrees or greater relative to each other, in particular 100 degrees or greater relative to each other, more particularly 105 degrees or greater relative to each other, most particularly 110 degrees or greater relative to each other.

16. A dose counter according to claim 1, wherein the first and second axes are disposed at an obtuse angle of 145 degrees or less relative to each other, in particular 135 degrees or less relative to each other, more particularly 125 degrees or less relative to each other, most particularly 120 degrees or less relative to each other.

17. A dose counter according to claim 1, wherein the second and worm axes are disposed at an obtuse angle of 95 degrees or greater relative to each other, in particular 100 degrees or greater relative to each other, more particularly 105 degrees or greater relative to each other, most particularly 110 degrees or greater relative to each other.

18. A dose counter according to claim 1, wherein the second and worm axes are disposed at an obtuse angle of 145 degrees or less relative to each other, in particular 135 degrees or less relative to each other, more particularly 125 degrees or less relative to each other, most particularly 120 degrees or less relative to each other.

19. An actuator for use with or as part of a dispenser, said actuator comprising a dose counter according to claim 1.

20. An actuator according to claim 19, wherein the dose counter is mounted within the interior of the actuator.

21. An actuator according to claim 19, wherein the actuator is an actuator for use with a canister including an aerosol container and a metering valve and wherein the dose counter is mounted within the interior of the actuator, such that, in use, the dose counter is generally positioned beneath the container near and/or around a nozzle block of the actuator; or wherein the actuator is an actuator for use with a canister including an aerosol container and a metering valve fitted with a dip tube and wherein the dose counter is mounted within the interior of the actuator, such that, in use, the dose counter is generally positioned above the container near and/or around a nozzle block of the actuator.

22. A dispenser comprising an actuator according to claim 19.

23. A dispenser comprising a dose counter according to claim 1.

24. A dispenser according to claim 23, wherein the dispenser is a metered dose dispenser, in particular a metered dose inhaler, more particularly a pressurized metered dose inhaler.

25. A dose counter according to claim 1, wherein the first and worm axes do not intersect.

* * * * *

UNITED STATES PATENT AND TRADEMARK OFFICE
CERTIFICATE OF CORRECTION

PATENT NO. : 8,814,035 B2  
APPLICATION NO. : 13/514192  
DATED : August 26, 2014  
INVENTOR(S) : Adam Stuart Page 1 of 1

It is certified that error appears in the above-identified patent and that said Letters Patent is hereby corrected as shown below:

IN THE CLAIMS

<u>Column 18</u>
Line 27, In Claim 8, after "worm" delete "flight".

Signed and Sealed this
Twenty-sixth Day of May, 2015

Michelle K. Lee
*Director of the United States Patent and Trademark Office*